United States Patent
Nguyen et al.

(10) Patent No.: US 7,450,986 B2
(45) Date of Patent: Nov. 11, 2008

(54) NON-INVASIVE METHOD AND APPARATUS FOR DETERMINING ONSET OF PHYSIOLOGICAL CONDITIONS

(75) Inventors: Hung Nguyen, Sydney (AU); Nejhdeh Ghevondian, North Ryde (AU)

(73) Assignee: Aimedics Pty Limited (AU)

( * ) Notice: Subject to any disclaimer, the term of this patent is extended or adjusted under 35 U.S.C. 154(b) by 439 days.

(21) Appl. No.: 10/469,814

(22) PCT Filed: Feb. 28, 2002

(86) PCT No.: PCT/AU02/00218

§ 371 (c)(1),
(2), (4) Date: Mar. 17, 2004

(87) PCT Pub. No.: WO02/069798

PCT Pub. Date: Sep. 12, 2002

(65) Prior Publication Data

US 2004/0167418 A1    Aug. 26, 2004

(30) Foreign Application Priority Data

Feb. 28, 2001    (AU)    ................................ PR3434

(51) Int. Cl.
*A61B 5/04* (2006.01)
(52) U.S. Cl. ........................ 600/513; 600/301
(58) Field of Classification Search ................ 600/300, 600/513, 515
See application file for complete search history.

(56) References Cited

U.S. PATENT DOCUMENTS

| 4,981,139 | A |   | 1/1991  | Pfohl .......................... 128/671 |
| 5,215,099 | A | * | 6/1993  | Haberl et al. ................ 600/515 |
| 5,680,866 | A |   | 10/1997 | Kangas et al. |
| 5,720,294 | A | * | 2/1998  | Skinner ....................... 600/300 |

(Continued)

FOREIGN PATENT DOCUMENTS

DE        4307545 A1      9/1994

(Continued)

OTHER PUBLICATIONS

Duck et al. "Teledyne Sleep Sentry: evaluation in pediatric patients for detection of nocturnal hypoglycemia." Diabetes Care. Nov.-Dec. 1983; 6(6):Abstract.*

(Continued)

*Primary Examiner*—Mark Bockelman
*Assistant Examiner*—Eric D Bertram
(74) *Attorney, Agent, or Firm*—Morgan, Lewis & Bockius LLP

(57) ABSTRACT

The invention relates to the modelling and design of early warning systems for detecting medical conditions using physiological responses. The device comprises sensors for monitoring physiological parameters such as skin impedance, heart rate, and QT interval of a patient, means for establishing when those parameters change, the rate of change of the parameters, and a neural network processor for processing the information obtained by the sensors. The neural network processor is programmed with a fast learning algorithm. When the neural network establishes that a physiological condition is present in the patient an alarm signal will be generated. The invention extends to a method of non-invasive monitoring of a person using a neural network programmed with a fast learning algorithm. A non-invasive hypoglycaemia monitor is specifically described.

19 Claims, 4 Drawing Sheets

U.S. PATENT DOCUMENTS 6,572,542 B1 *   6/2003   Houben et al. .............. 600/300

FOREIGN PATENT DOCUMENTS

| EP | 0627194 | | 7/1994 |
|---|---|---|---|
| EP | 699413 | A1 | 3/1996 |
| EP | 1127543 | A1 | 8/2001 |
| GB | 2281780 | | 3/1995 |
| WO | WO 92/03966 | A1 | 3/1992 |
| WO | WO9741772 | | 11/1997 |

OTHER PUBLICATIONS

Supplementary European Search Report dated Dec. 20, 2006, 3pp.

* cited by examiner

NON-INVASIVE METHOD AND APPARATUS FOR DETERMINING ONSET OF PHYSIOLOGICAL CONDITIONS

This application claims priority to and incorporates by reference PCT application PCT/AU02/00218, filed Feb. 28, 2002, which claimed priority to Australian patent application PR3434, filed Feb. 28, 2001.

FIELD OF THE INVENTION

The present invention relates to the modelling and design of early warning systems using physiological responses. In particular such systems can be used for early detection of medical conditions, a non-invasive hypoglycaemia monitor for example. Although this specification concentrates on a system and method for the detection of hypoglycaemia, it should be understood that the invention has wider application.

BACKGROUND OF THE INVENTION

Hypoglycaemia is the most common complication experienced by patients with insulin dependent diabetes mellitus. Its onset is characterised by symptoms which include sweating, tremor, palpitations, loss of concentration and tiredness. Although the majority of patients can use these symptoms to recognise the onset of hypoglycaemia and take corrective action, a significant number of patients develop hypoglycaemic unawareness and are unable to recognise the onset of symptoms.

Concerning hypoglycaemia, the blood glucose in men can drop to 3 mmol/L after 24 hrs of fasting and to 2.7 mmol/L after 72 hrs of fasting. In women, glucose can be low as 2 mmol/L after 24 hrs of fasting. Blood glucose levels below 2.5 mmol/L are almost always associated with serious abnormality. Hypoglycaemia in diabetic patients has the potential to become dangerous. In many cases of hypoglycaemia, the symptoms can occur without the awareness of the patient and at any time, eg. while driving or even during deep sleep. In severe cases of hypoglycaemia, the patient can lapse into a coma and die. Nocturnal episodes are also potentially dangerous and have been implicated when diabetic patients have been found unexpectedly dead in bed. Hypoglycaemia is one of the complications of diabetes most feared by patients, on a par with blindness and renal failure.

Current technologies used for diabetes diagnostic testing and self-monitoring are known. For example, glucose meter manufacturers have modified their instruments to use as little as 2 µl of blood and produce results in under a minute. However, devices which require a blood sample are unsatisfactory in that the sample is painful to obtain, and continuous monitoring is not possible.

There are only a few manufacturers who have produced non-invasive blood glucose monitoring systems. The Diasensor 1000 from Biocontrol Technology Inc. uses near-infrared technology and multivariate regression to estimate blood glucose levels. The system is very expensive, it has to be individually calibrated to each patient, it has to be recalibrated every three months, and the calibration process takes up to seven days. The GlucoWatch monitor from Cygnus is designed to measure glucose levels up to three times per hour for 12 hours. The AutoSensor (the disposable component) which is attached to the back of the GlucoWatch monitor and adheres to the skin will provide 12 hours of measurement. The product uses reverse iontophoresis to extract and measure glucose levels non-invasively using interstitial fluid. It requires 12 hours to calibrate, only provides 12 hours of measurement, requires costly disposable components, and the measurement has a time delay of 15 minutes. Another device, the Sleep Sentry, monitors perspiration and a drop in body temperature to alert the patient to the onset of hypoglycemia. In studies of patients admitted for overnight monitoring it was found to be unreliable in between 5% and 20% of cases.

During hypoglycaemia, the most profound physiological changes are caused by activation of the sympathetic nervous system. Among the strongest responses are sweating and increased cardiac output. Sweating is centrally mediated through sympathetic cholinergic fibres, while the change in cardiac output is due to an increase in heart rate and increase in stroke volume.

It is an object of the invention to provide a non-invasive method of detecting medical conditions in patients, which is relatively accurate and relatively inexpensive to use, and will trigger an alarm signal within an acceptable time delay from when a condition which is being monitored for presents itself

SUMMARY OF THE INVENTION

According to a first aspect of the invention there is provided a non-invasive method of determining the presence or onset of a physiological condition in a person comprising the steps of:

continuously monitoring two or more of at least the following parameters of the patient: skin impedance, heart rate, QT interval, and mean or peak frequency of the alpha wave;

establishing whether one or more of those monitored parameters changes, and if so, the rate of change of that parameter or parameters;

feeding data obtained in the first two steps into a neural network processor programmed with a fast learning algorithm; and causing an alarm signal to be triggered when said neural network establishes conditions which suggest the presence or imminent onset of said physiological condition.

The monitoring of the heart rate and QT interval is preferably done with a ECG. The monitoring of the alpha wave is preferably done with an EEG. The fast learning algorithm may have either a magnified gradient function, or an optimal gradient function, or may be a robust sliding mode learning algorithm.

The invention extends to apparatus for generating an alarm when a physiological condition is present or imminent in a person, said apparatus comprising:

sensors for sensing at least two of the skin impedance, heart rate, QT interval, and mean or peak frequency of the alpha wave;

means for establishing when one or more of the sensed parameters changes and when so established, the rate of change of said changed parameters, a neural network linked to said sensors and said means so as to receive a substantially continuous data stream from said sensors and said means, the neural network being programmed with a fast learning algorithm and adapted to establish when the sensed parameters, and any change to those parameters, for a particular person are such as to indicate the presence or imminent onset of said physiological condition, and alarm means linked to said neural network adapted to be triggered when the presence or imminent onset of said physiological condition is established.

The apparatus may include a magnified gradient function, an optimal gradient function, or is a robust sliding mode learning algorithm.

DETAILED DESCRIPTION OF THE INVENTION

Figure 1:
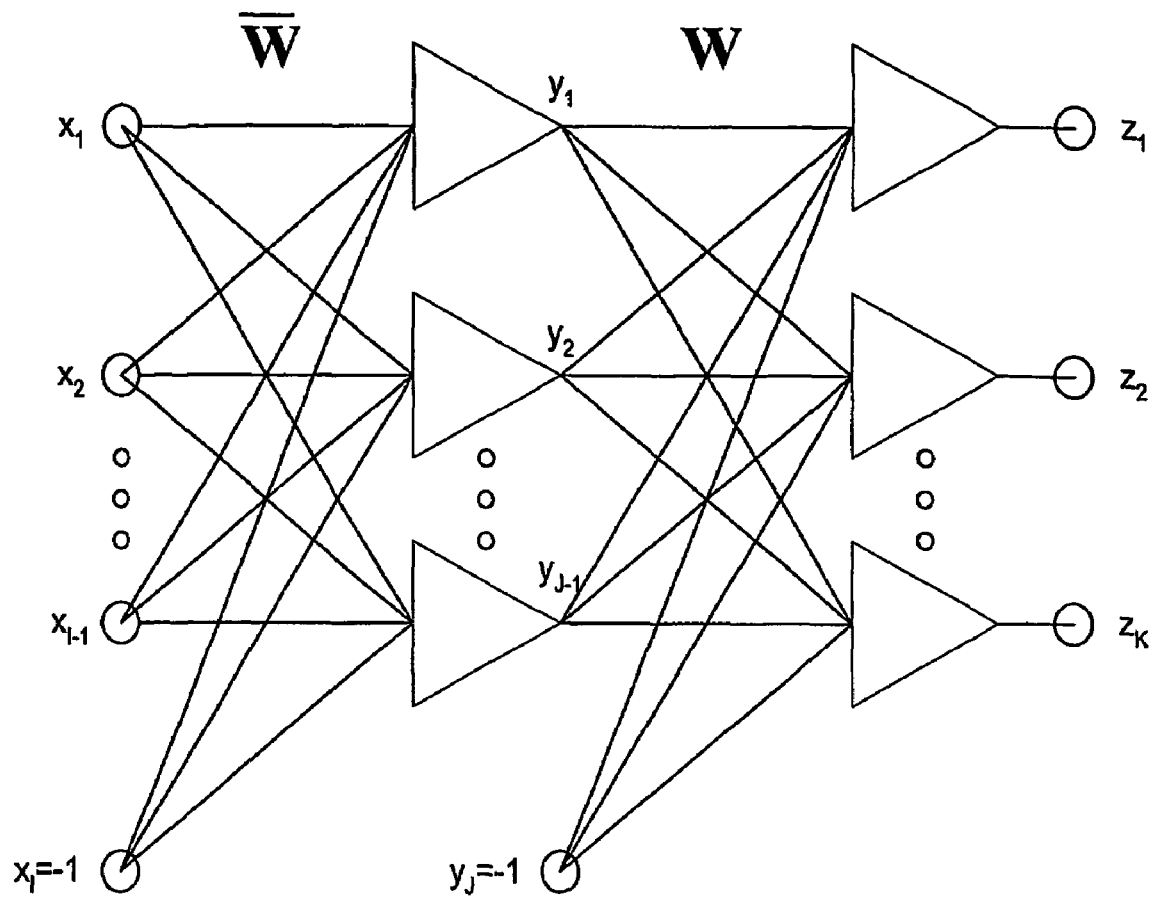
FIG. 1 shows the basic structure of a two-layer feed forward neural network.

In the development of the device, analysis of the effectiveness of skin impedance, ECG (in particular heart rate and QT interval) and EEG by means of a robust neural network provides a novel basis for early detection of a medical condition such as hypoglycemia as well as an indirect measurement of blood glucose levels. There are numerous factors which can affect the accuracy with which a medical condition is precluded such as environment conditions, stress, and the like. The device should be capable of differentiating between effects caused by environmental conditions and those which indicate the presence of or onset of a particular medical condition.

The possibility of hypoglycaemia induced arrythmias, and experimental hypoglycaemia has been shown to prolong QT intervals and dispersion in both non-diabetic subjects and in those with Type 1 and Type 2 diabetes. Another important physiological change is that a slowing of the a rhythm in EEG (8-13 Hz) in response to hypoglycaemia appears at blood glucose values of approximately 2.5 mmol/L and is the earliest abnormality.

In broad terms, a device which is capable of initiating and correctly interpreting a wide range of physiological signals could be used for the detection of conditions such as hypoglycaemia, hyperglycaemia, or may be used to provide indirect measurement of blood glucose levels. It may also be used for the detection of sudden infant death syndrome, chronic stress, sleep disorders and driver fatigue for example. Indeed, other medical conditions which present themselves by a range of different physiological indications could be detected using the method and apparatus of the invention. Because physiological signals differ from patient to patient it is important that a device is able to "learn" when a particular set of signals represent the onset or presence of a medical condition in a particular patient, and disregard false signals which might be caused by environmental or other factors.

There are many different ways to implement the signal sensing and signal conditioning for the device. One implementation strategy can be described as follows.

Skin moisture (sweating) can be measured using skin impedance monitoring. A concentric type electrode may be used which contains an outer passive electrode (10mm inner and 20mm outer diameter) and an inner electrode (5mm diameter). A sinusoidal constant current source of 100kHz 10 µA may be applied by a Wien bridge oscillator to the inner electrodes, and a voltage produced in accordance to the skin impedance, at the outer electrode. The signal from the outer electrode may be amplified by an instrumentation amplifier, passed through a Butterworth low-pass filter (cut-off freq =140kHz) and fed through an AC-DC converter to produce a DC signal proportional to the skin impedance.

The ECG may be achieved by placing three Ag-AgCl electrodes 12 in a LeadII configuration on the patient's chest. The signal obtained from the electrodes may then be amplified using an instrumentation amplifier with gain of 10 and CMRR >100dB at 100Hz. This feeds through a high-pass filter with cutoff frequency of 0.5Hz. A second stage non-inverting amplifier may be added to provide a gain of 100. To obtain a reliable heart rate of the patient, a bandpass filter may be used, to detect the QRS complex of the ECG signal. A threshold circuit together with a comparator may be used to reliably detect the R slope. The QT interval, on the other hand is a clinical parameter which can be derived from the ECG signal. During hypoglycemia, the QT interval increases. QT measurement requires the identification of the start of QRS complex and the end of the T wave. The intersection of the isoelectric line and a tangent to the T wave can be used to measure the QT interval.

EEG signals may be obtained using a pair of Ag-AgCl electrodes 18 and 20 on $O_1$ and $O_2$ sites on the posterior cortex. The conditioning circuitry includes a two op-amp instrumentation amplifier to obtain high overall gain. Low voltage and current noise CMOS amplifiers may be used for EEG recordings to reproduce these signals for diagnostic purposes. In this instrumentation amplifier configuration, an integrator in the feedback loop provides a low overall gain for the low-frequency input signals. For high resolution, the digital sampling rate per channel may be 256 Hz and data may be stored in one-second epochs. Signals may be analysed using Fast Fourier Transform (FFT). The mean frequency or the peak frequency of the a wave in EEG can then be derived.

The monitoring for hypoglycaemia and blood glucose level is difficult because of imperfections caused by possible conflicting or reinforcing responses from skin impedance, ECG and EEG. This conflicting information is handled in the framework of a robust neural network in order to obtain accurate determinations from a complex uncertain non-linear physiological system.

For hypoglycaemia detection using a combination of four variables (skin impedance, heart rate, QT interval and mean or peak frequency of the α wave) the analysis is akin to a black box belonging to a given class of nonlinear systems. A neuro-estimator is suitable for complex estimates. A neuro-estimator may be embedded in an EEPROM of the system to monitor hypoglycaemia episodes in patients. This neural network has a multilayer feedforward neural network structure with one input layer, one hidden layer and one output layer as shown in FIG. 1. Essentially, this neural network is trained using a learning algorithm in which synaptic strengths are systematically modified so that the response of the network will increasingly approximate the blood glucose status given by the available qualitative data.

The back-propagation (BP) algorithm is a widely applied multilayer neural-network learning algorithm. Unfortunately, it suffers from a number of shortcomings. One such shortcoming is its slow convergence. A preferred system will implement real-time learning so as to be able to adapt to the physiological signals of individual patients.

The learning algorithms for updating the weight matrices may be based on a magnified gradient algorithm or a sliding mode strategy. The gradient descent back-propagation (BP) learning algorithm for updating the weight matrices, the error signal terms for output layer and hidden layer respectively can be found from:

$$\delta_k = -\frac{\partial E}{\partial v_k} = (R_k - z_k)\frac{\partial z_k}{\partial v_k} \quad \overline{\delta}_j = -\frac{\partial E}{\partial \overline{v}_j} = \frac{\partial y_j}{\partial \overline{v}_j}\sum_{k=1}^{K}\delta_k w_{kj}$$

-continued $$W^* = W - \eta \frac{\partial E}{\partial W} = W + \eta \delta y' \quad \overline{W}^* = \overline{W} - \eta \frac{\partial E}{\partial \overline{W}} = \overline{W} + \eta \overline{\delta} x'$$

where $\delta_k$ and $\overline{\delta}_j$ are error signal terms for the output layer and hidden layer respectively:

$W^*$ and $\overline{W}^*$ are weight matrices and may be based on a magnified gradient algorithm or a sliding mode strategy;

$R_k$ represents the reference blood glucose value or hypoglycemia classification at node k;

$v_k$ represents the excitation of output neuron k; and $\overline{v}_j$ represents the excitation of the hidden neuron j.

For faster network convergence suitable for real-time learning, a magnified gradient function (MGF) in adaptive learning can be used, where the error signal terms for output layer and hidden layer can be magnified with a constant S (usually between 1 and 5):

$$\delta_j = -\frac{\partial E}{\partial \overline{v}_k} = (R_k - z_k) \left( \frac{\partial z_k}{\partial v_{kj}} \right)^{\frac{1}{S}} \quad \overline{\delta}_j = -\frac{\partial E}{\partial \overline{v}_j} = \left( \frac{\partial y_j}{\partial \overline{v}_j} \right)^{\frac{1}{S}} \sum_{k=1}^{K} \delta_k w_{kj}$$

$$\left| \left( \frac{\partial E}{\partial t} \right)_{MGF} \right| - \left| \left( \frac{\partial E}{\partial t} \right)_{BP} \right| > 0$$

MGF-PROP retains the gradient-descent property and the convergence rate of MGF-PROP is faster than that of BP. This algorithm can be implemented in real-time relatively easily.

Similar to the above solution, it is also possible to develop a back propagation algorithm based on sliding mode for updating the weight matrices. This type of algorithm should be faster as the rate of convergence can be controlled, and is more robust against parameter uncertainty and strong disturbances, as the error will be forced to slide along a pre-determined hyperplane.

In order to detect hypoglycaemia episodes reliably, it is not a simple matter of just using a combination of the above-mentioned parameters: skin impedance, heart rate, QT interval, mean or peak frequency of the $\alpha$ wave. The main difficulty is different patients have different base values of these parameters. In addition, these base values may vary from day to day.

False detection may arise from other environmental or personal conditions which could cause similar variations in sweating and heart rate such as the occurrence of nightmares, sudden change in weather, etc. Avoidance of false detection is important if the system is to be relied on by sufferers of acute or life threatening conditions.

As a consequence, the main parameters used for the detection of hypoglycaemia are not only skin impedance, heart rate, QT interval or mean/peak frequency of the $\alpha$ wave, but also their rates of change. The additional parameters are the rates of change in skin impedance, heart rate, QT interval and mean/peak frequency of the $\alpha$ wave. Other important parameters are the time constants associated with these physiological responses. Rates of changes and the time constants inherent in physiological responses are important factors which can be used to reject or minimise false detection.

It is possible to model the dynamic neural network which is used to estimate blood glucose levels as:

$$\frac{dx}{dt} = f(x) + g(x) \cdot u$$

$$z = \sigma[W \cdot \phi(\overline{W} x)]$$

where x is the state of the neural network and $\sigma$ and $\phi$ are sigmoidal vector functions. Note that x contains the skin impedance, heart rate, QT interval, peak frequency of the $\alpha$ wave, and their rates of changes. The nonlinear functions $f(x)$ and $g(x)$ contain the time contants associated with the state vector x. In other words, this equation describes how fast the important physiological parameters such as the skin impedance, heart rate, QT interval, and peak a frequency respond to a reduction of blood glucose levels.

The above model also allows the identification of model variations and disturbances to ensure that the convergence of the leaning algorithm is assured. This is important for providing real-time neural network adaptation to a specific patient for the detection of a physiological condition such as hypoglycaemia under various conditions.

Using the above important main parameters for hypoglycaemia detection, the learning algorithms for updating the weight matrices based on a magnified gradient algorithm or a sliding mode strategy allows the neural network to adapt on-line to a particular patient very effectively or to provide robust estimation in the presence of disturbances (initial state, system and observation noises) to minimise false detection.

Figure 2:
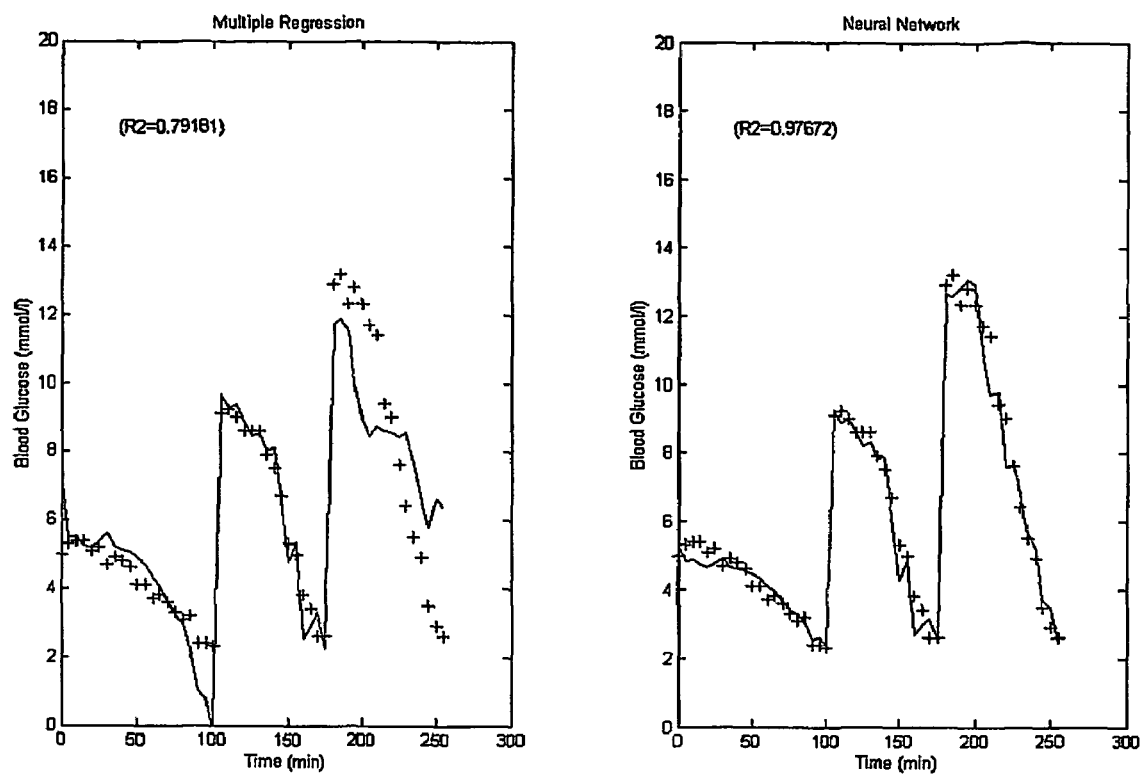
FIG. 2 shows blood glucose level estimations using multiple regression (left) and neural network (right) for three diabetic patients.
Figure 3:
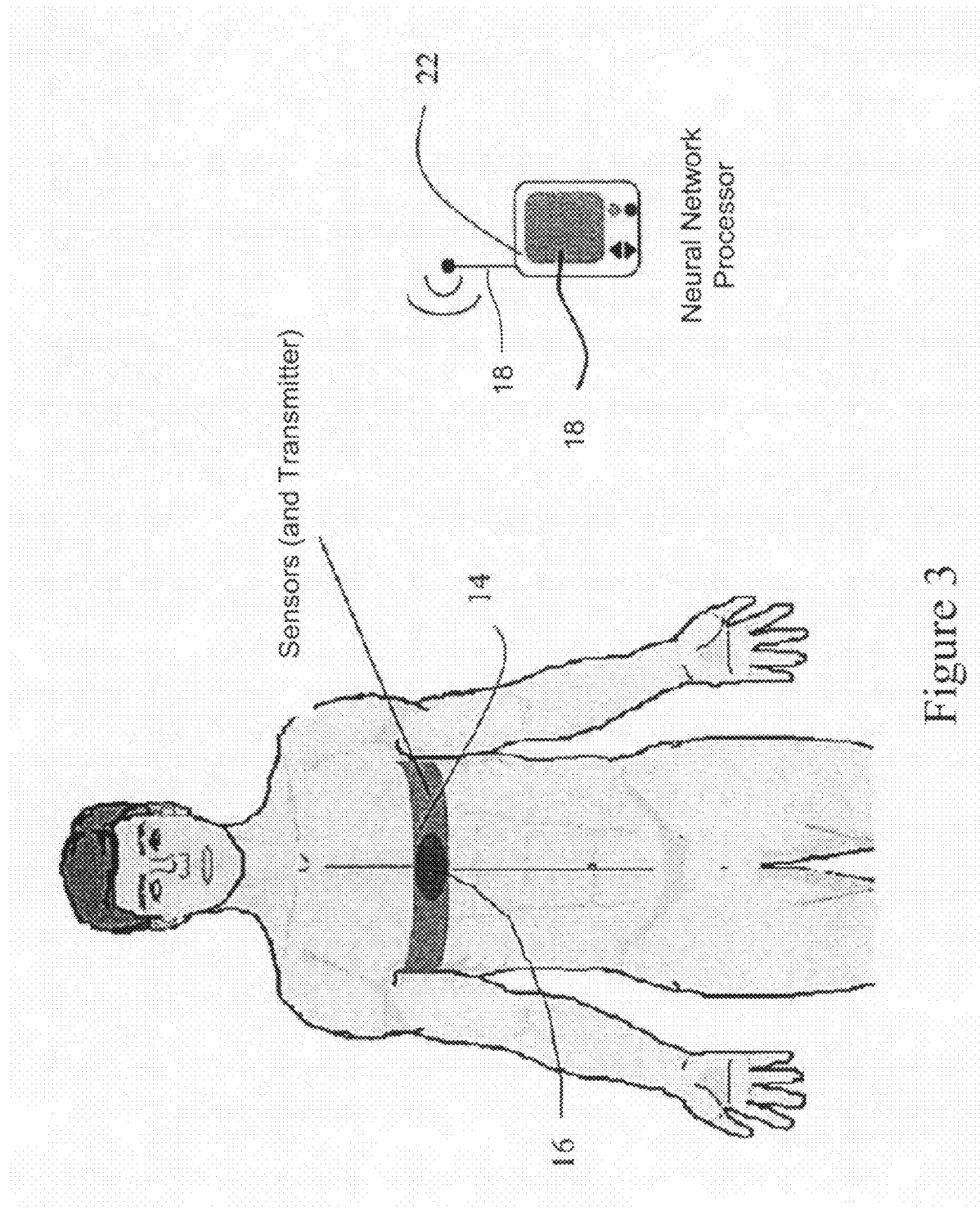
FIG. 3 shows a block diagram of an apparatus for generating an alarm when a physiological condition is present or imminent in a person.
Figure 4:
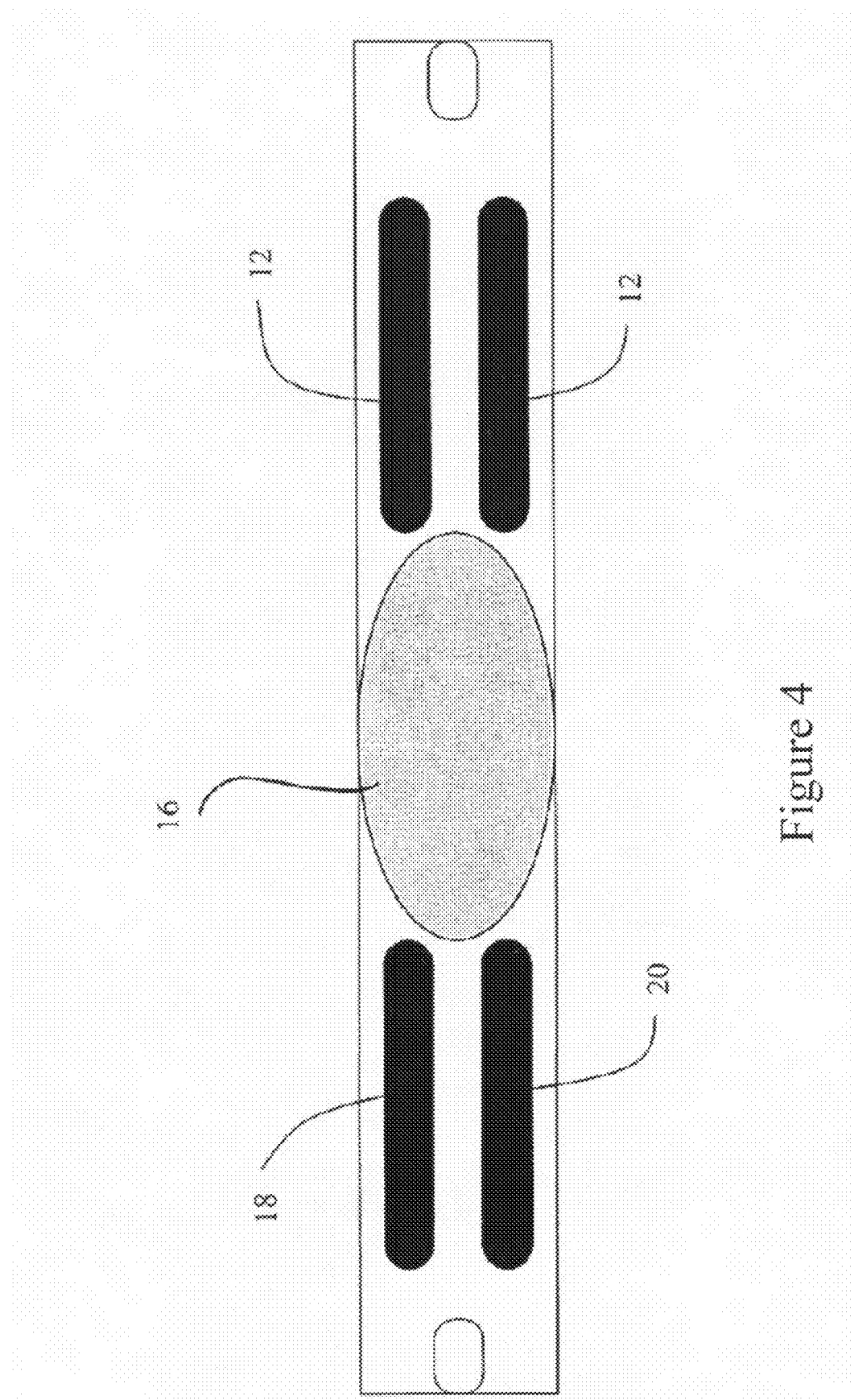

A combination or all of these parameters are fed into a generic neural network for the detection of hypoglycaemia or the estimation of blood glucose levels. FIG. 2 shows the estimation of blood glucose levels using only skin impedance and heart rate for three diabetic patients. In FIG. 2, the result of a multiple regression technique used to evaluate corresponding blood glucose levels is shown on the left with good correlation ($R^2=0.792$), and the result of a trained neural network is shown on the right with a very strong correlation ($R^2=0.977$).

It is envisaged that the device, once properly trained, should be capable of not only determining the onset or presence of a condition, but also bale to assign a value to that condition. Thus, for example, if the device is able to accurately estimate actual blood glucose levels, then the patient should be able to use that estimation to modify quantum and timing of medication.

In practice, a trained neural network would be obtained off-line for many patients, but the described neural network should have the ability to adapt to a particular patient. This hypoglycaemia monitor can quickly fine tune the neural network for better estimation of blood glucose levels or hypoglycaemia conditions, using either the magnified gradient function back propagation technique (MGF-PROP) or the sliding mode back propagation technique (SM-PROP). Both of these two techniques can be implemented in real-time with very fast convergence.

It is envisaged that communication between the sensors and the processor 19 may be via a telemetric system. Radio frequency transmitters 16 and receivers 17 or transceivers (typically 433 MHz or 2.4GHz) may be used.

The alarm may be of any convenient type, and might comprise a simple radio alarm 22 a signal transmitted to a monitoring station, or the like.

It is also preferred that data transmitted from the sensors will be continuously logged. The system may be interfaced with a PC which will continuously log the relevant data using a data management system such as Labview.

Clearly the invention can vary from that described herein without departing from the scope of the invention. In particular the fast learning algorithm need not be of the type described herein, but any fast learning algorithm that is able to provide substantially real time analysis of multiple data streams in the manner described herein could be used.

The invention claimed is:

1. A non-invasive method of determining the value, presence or onset of a hypoglycemia condition in a patient known to be susceptible to hypoglycemia comprising the steps of:
    determining base parameters of a patient at which the onset of hypoglycemia is likely to occur, said base parameters including: skin impedance, heart rate, QT interval, and mean or peak frequency of an alpha wave;
    continuously monitoring the patient's parameters comprising: skin impedance, heart rate, QT interval, and mean or peak frequency of the alpha wave;
    establishing whether one or more of those monitored parameters changes, and if so, the rate of change of that parameter or parameters;
    feeding data obtained from said monitoring and said establishing into a neural network processor programmed with a fast learning algorithm;
    comparing the data to the base parameters for that patient; and
    based on said comparing, causing a signal to be generated either when said neural network establishes conditions that suggest a presence or imminent onset of a hypoglycemic condition, or when said neural network has estimated a value of said hypoglycemic condition.

2. The non-invasive method according to claim 1 wherein the monitoring of the heart rate and QT interval is done with an ECG.

3. The non-invasive method according to claim 1 wherein the monitoring of the alpha wave is done with an EEG.

4. The non-invasive method according to claim 1 wherein the fast learning algorithm has either a magnified gradient function or an optimal gradient function.

5. The non-invasive method according to claim 1 wherein the fast learning algorithm is a robust sliding mode algorithm.

6. An apparatus for generating an alarm when hypoglycemia is present or imminent in a patient known to be susceptible to hypoglycemia, said apparatus comprising:
    sensors for sensing a patient's parameters comprising: skin impedance, heart rate, QT interval, and mean or peak frequency of an alpha wave;
    means for establishing when one or more of the sensed parameters changes and when so established, a rate of change of that parameter or parameters;
    a neural network linked to said sensors and said means for establishing so as to receive a substantially continuous data stream from said sensors and said means for establishing, the neural network being programmed with a fast learning algorithm and adapted to establish when the sensed parameters, and any change to those parameters, for a particular person are such as to indicate a presence or imminent onset of a-hypoglycemic condition;
    and alarm means linked to said neural network and adapted to be triggered when the presence or imminent onset of said hypoglycemic condition is established.

7. The apparatus according to claim 6 wherein the fast learning algorithm has either a magnified gradient function or an optimal gradient function.

8. The apparatus according to claim 6 wherein the fast learning algorithm is a robust sliding mode algorithm.

9. The apparatus according to claim 6 wherein the sensors used to sense the heart rate and QT interval include an ECG.

10. The apparatus according to claim 6 wherein the sensors used to sense the mean or peak alpha wave are an EEG.

11. The apparatus according to claim 6 wherein data is transmitted between the sensors and the neural network by radio frequency.

12. The apparatus according to claim 6 wherein the apparatus is adapted to estimate an actual value of said hypoglycemic condition of the patient.

13. The apparatus according to claim 12 wherein the hypoglycemic condition which the apparatus is adapted to estimate is a blood glucose level of the patient.

14. An apparatus for generating an alarm when hypoglycemia is present or imminent in a patient known to be susceptible to hypoglycemia, said apparatus comprising:
    sensors for sensing a patient's parameters comprising: skin impedance, heart rate, QT interval, and mean or peak frequency of an alpha wave;
    a comparator that establishes when one or more of the sensed parameters changes and when so established, a rate of change of that parameter or parameters;
    a neural network linked to said sensors and said comparator so as to receive a substantially continuous data stream from said sensors and said comparator, the neural network being programmed with a fast learning algorithm and adapted to establish when the sensed parameters, and any change to those parameters, for a particular person are such as to indicate a presence or imminent onset of a-hypoglycemic condition;
    and an alarm linked to said neural network and adapted to be triggered when the presence or imminent onset of said hypoglycemic condition is established.

15. The apparatus according to claim 14 wherein the fast learning algorithm has either a magnified gradient function or an optimal gradient function.

16. The apparatus according to claim 14 wherein the fast learning algorithm is a robust sliding mode algorithm.

17. The apparatus according to claim 14 wherein the sensors used to sense the hear rate and QT interval parameters include an ECG.

18. The apparatus according to claim 14 wherein the sensors used to sense the mean or peak alpha wave parameters are an EEG.

19. The apparatus according claim 14 wherein data is transmitted between the sensors and the neural network by radio frequency.

* * * * *